United States Patent

Segawa

[11] Patent Number: 5,863,287
[45] Date of Patent: Jan. 26, 1999

[54] REMOVABLE PROTECTOR SHEATH FOR USE WITH ENDOSCOPIC INSERTION INSTRUMENT

[75] Inventor: Yoichi Segawa, Omiya, Japan

[73] Assignee: Fuji Photo Optical Co., Ltd., Omiya, Japan

[21] Appl. No.: 725,712

[22] Filed: Oct. 4, 1996

[30] Foreign Application Priority Data

Oct. 4, 1995 [JP] Japan .................................. 7-279883

[51] Int. Cl.$^6$ ........................................................ A61B 1/04
[52] U.S. Cl. ........................................... 600/121; 600/133
[58] Field of Search ................................... 600/121, 122, 600/123, 124, 125, 153, 156, 157, 158, 138, 139, 133

[56] References Cited

U.S. PATENT DOCUMENTS

| | | | |
|---|---|---|---|
| 5,105,800 | 4/1992 | Takahashi et al. | 600/121 |
| 5,203,781 | 4/1993 | Bonati et al. | 606/15 |
| 5,415,157 | 5/1995 | Welcome | 600/121 |
| 5,575,756 | 11/1996 | Karasawa et al. | 600/121 X |

FOREIGN PATENT DOCUMENTS

| | | | |
|---|---|---|---|
| 349479 | 1/1990 | European Pat. Off. | 600/121 |
| 3508833 | 9/1986 | Germany | 600/121 |
| 4-361731 | 12/1992 | Japan | 600/121 |

*Primary Examiner*—Beverly M. Flanagan
*Attorney, Agent, or Firm*—Oblon, Spivak, McClelland, Maier & Neustadt, P.C.

[57] ABSTRACT

A removable protector sheath for an endoscopic insertion instrument of the type having an endoscopic insertion rod extended out from a manipulating or gripping head and including, successively from its proximal end on the side of the manipulating head, a rigid rod section, a flexible rod section, an angle section and a distal end section. The protector sheath is provided with a hollow tubular case enshrouding at least the flexible rod section, angle section and distal end section of the insertion rod. The tubular case is provided with stopper means for releasably stopping the protector sheath on the insertion rod by engagement with a trap means provided on the rigid rod section or on the manipulating head of the endoscopic insertion instrument.

6 Claims, 5 Drawing Sheets

REMOVABLE PROTECTOR SHEATH FOR USE WITH ENDOSCOPIC INSERTION INSTRUMENT

BACKGROUND OF THE INVENTION

1. Field of the Art

This invention relates to endoscopic insertion instruments of the sort which has an endoscopic insertion rod extended out from a manipulating or gripping head and which includes, successively from a proximal end, a rigid rod section, a flexible rod section, an angle section and a distal end section as in the case with vaginal endoscopes, and more particularly to a removable protector sheath to be fitted on such an endoscopic insertion instrument to prevent buckling or similar damages to the flexible rod section particularly in its end portions connected to a rigid rod section of the insertion instrument.

2. Prior Art

Generally, endoscopic insertion instruments are largely constituted by a manipulating or gripping head and an insertion rod extended out from the manipulating head for insertion into an internal canal of a patient or other intracavitary portions to be examined. By the nature of the insertion instrument, endoscopes can be categorized into a rigid or hard type employing an insertion instrument in the form of a rigid structure, and a flexible or soft type employing an insertion instrument in the form of a flexible structure except for an angle section and a distal end section which are connected to the fore end of a flexible insertion rod. Further, in some endoscopes, the insertion instrument is provided with a rigid rod section of a certain length from its proximal end, which is connected to a manipulating head, in addition to a flexible rod section, an angle section and a rigid distal end section as mentioned above.

Among various types of endoscopes with different insertion rod constructions, the vaginal endoscope is typical of the endoscopes which are provided with a rigid-flexible insertion instrument having a rigid rod section at a proximal end of an insertion rod or between a flexible rod section and a manipulating head of the instrument. In the case of a vaginal endoscope, by its nature, an actual insertion length is relatively short as compared with the total length of the insertion rod, which is usually provided in an ample length to permit the operator to handle the manipulating head at a suitable distance from the patient body. In this connection, the operator would face problems of instability and inferior maneuverability of the instrument if the insertion rod were made flexible over its entire length a major proportion of which always remains outside the patient body. Therefore, it has been the general practice to use a rigid pipe structure or the like in a proximal portion of the insertion rod between a manipulating head and a flexible rod section and to interpose an angle section between the flexible insert portion and a rigid distal end section thereby to turn endoscopic observation means on the rigid distal end section into directions of particular interest.

Once introduced into patient body for examination or diagnostic purposes, the endoscopic insertion instruments is contaminated by contact with body fluids and therefore needs to be washed clean after each use. In this regard, the general procedure has been to wash used endoscopic insertion instruments by immersion in a cleaning liquid in a washing sink which is equipped with a clean water tap along with a closed spent water drainage system exclusively for this purpose. Washing equipments of this sort are normally installed in a cleaning room or station other than an endoscopic examination room or rooms, so that used endoscopes have to be collected from an examination room or rooms and taken to the cleaning station by hand for immersion in the cleaning liquid.

The endoscopic insertion rod of this sort contains at least a light guide and an image transfer means, for example, an image guide in the case of an optical endoscope or a signal cable in the case of an electronic endoscope having a solid-state image sensor fitted in an observation window at the distal end of the insertion rod. In many cases, the insertion rod further accommodates a biopsy channel for insertion of bioptic instruments such as forceps or the like, and a fluid conduit tube for feeding a fluid medium to a fluid outlet at the distal end of the insertion rod. In the flexible rod portion of the instrument, generally all of these component parts are fitted in a tubular flexible structure, which is constituted by, for example, one or a plural number of layers of helical coil tubes, metal wire netting wrapped around the helical coils tubes, and an outer skin layer formed on the exterior side of the metal wire netting. Any way, the flexible rod section of the insertion instrument is arranged in such a manner as to have a relatively high degree of flexibility in order to guarantee free bending flexures in arbitrary directions along paths of insertion, and directly connected to rigid rod sections of the insertion instrument at its fore and rear ends. Therefore, the rigidity of the insertion rod changes drastically across the joints of the flexible and rigid rod sections.

After use, a contaminated endoscope is picked up by one of cleaning staff and, for an immersed cleaning treatment in a washing sink as mentioned hereinbefore, taken to a cleaning room or station where cleaning equipments are installed, gripping the endoscope particularly by a rigid rod section which has not been introduced into patient body, for example, by a manipulating head portion, a rigid rod section of the insertion rod and/or a light guide cable connected to the manipulating head of the endoscope, while paying attention not to touch either insertion rod portions forward of the flexible rod portion, which have been contaminated with body fluids, including the rigid tip end portion at the distal end of the flexible rod section nor rigid rod portions immediately adjoining the flexible rod section. In handling contaminated endoscopes in this manner in a post-examination stage, there are always possibilities of the tip end section of the insertion rod or other fragile or vulnerable part of the endoscope being hit against hard surfaces of nearby objects or structures or against walls or other parts of the washing sink.

When hit against a sink wall or other hard surfaces, rigid portions of an endoscopic insertion rod would not sustain any material damages unless the collisional impact is of an extraordinarily large magnitude, in contrast to the flexible rod portions which are easily bent by collisional impacts. Especially at a joint of flexible and rigid rod sections, which have conspicuously different rigidities, it is very likely that the flexible side of the rod be abruptly bent at the time of collision and as a result forcibly deformed or buckled to an abnormal degree. This is very much so in the case of a vaginal endoscope with a relatively narrow flexible rod section on the insertion rod, employing helical coils of lower strength as a flexible structural for the flexible section. When bent forcibly, a narrow flexible rod portion of this nature is susceptible to buckling or deformation to such a degree as would cause breakage or other damages to the component parts which are fitted in the flexible rod section, for example, breakage of fiber optics of a light guide or of an image guide.

SUMMARY OF THE INVENTION

In view of the foregoing situations, it is an object of the present invention to provide a removable protector sheath for use with an endoscopic insertion rod, which can suitably protect fore end portions of an endoscopic insertion rod against collisional impacts while being carried for transfer from one place to another, for example, from an examination room to a cleaning room or station.

It is another object of the present invention to provide a removable protector sheath of the sort as mentioned above, which can protect a flexible rod section of an endoscopic insertion rod against buckling damages particularly in its end portions adjoining rigid sections of the endoscopic insertion rod, while permitting facilitated disinfection of insertion rod portions to be introduced into patient body.

It is still another object of the present invention to provide a removable protector sheath of the sort as mentioned above, which can keep contaminated portions of an endoscopic insertion rod from transferring contaminants to nearby objects by direct contact therewith or by collision thereagainst.

In accordance with the invention, the above-stated objectives are achieved by the provision of a removable protector sheath for use on an endoscopic insertion instrument of the sort having, successively from its proximal to fore end, a manipulating or gripping head, a rigid rod section, a flexible rod section, an angle section and a distal end section, the protector sheath having a tubular body of such a length as to be able to enshroud at least the flexible rod section, angle section and distal end section of the endoscopic insertion instrument, and provided with a stopper means at a proximal end for detachably stopping the protector sheath on the rigid rod section or on the manipulating head of the endoscopic insertion instrument.

From the standpoint of protecting an endoscopic insertion instrument while the endoscope is being carried for transfer from one place to another, the protector sheath is preferred to be able to enshroud at least a flexible rod section, angle section and distal end section of an endoscopic insertion instrument, keeping these sections from directly contacting or colliding against nearby objects or structures. In this regard, preferably the body of the protector sheath is formed of a rigid material such as metal, hard plastics or the like or a resilient material such as rubber or the like. In case of a resilient material, however, it should have a certain degree of stiffness to prevent transmission of collisional impacts to the enshrouded insertion rod.

Further, preferably the protector sheath is releasably fixable to a rigid rod section or to the manipulating or gripping head of the endoscopic insertion instrument. Among various fixation means such as threaded engagement, bayonet, set screws and so forth, it is preferable to employ a stopper means which can be pushed into locked and released positions by one and single action.

In case the protector sheath is in the form of a tubular case which is completely closed except for one end which serves as an entrance and an exit for an endoscopic insertion rod, it can be used as a disinfectant reservoir container for the endoscopic insertion rod. In such a case, the protector sheath body is provided with a fluid inlet port in the vicinity of its open proximal end, which fluid inlet port is disconnectibly connectable, for example, to a disinfectant injector or pumping means. In case the protector sheath is used as a disinfectant container, however, it becomes necessary to put on and off the protector sheath before and after washing the endoscopic insertion rod. If this is troublesome, however, the protector sheath may be formed in a double-sheath structure which is composed of an inner sheath perforated with a number of cleaning liquid circulating holes in its girder within a limited range which would not impair the function of protecting the flexible rod section, angle section and distal end section of the endoscopic insertion instrument against collisional impacts, and an outer sheath to be fitted on the first sheath and hermetically closable to hold a disinfectant fluid in a sealed state therein.

BRIEF DESCRIPTION OF THE DRAWINGS

The above and other objects, features and advantages of the invention will become apparent from the following particularly description of the invention, taken in conjunction with the accompanying drawings which show by way of example some preferred embodiments of the invention and in which.

DESCRIPTION OF PREFERRED EMBODIMENTS

Hereafter, the invention is described particularly by way of its preferred embodiments with reference to the accompanying drawings.

Figure 1:
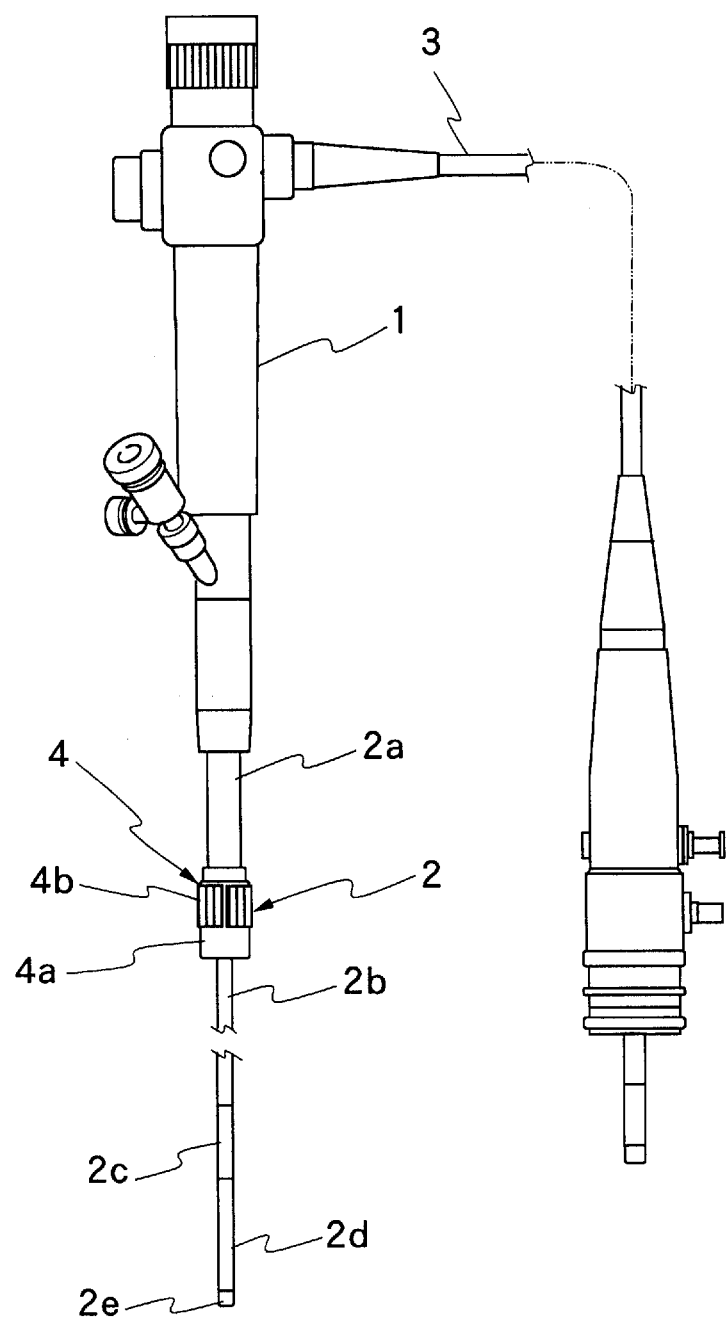
FIG. 1 is a schematic view of a vaginal endoscope, shown as an example typical of endoscopes to which the protector sheath according to the present invention is applicable.

Shown in FIG. 1 is the general layout of an insertion instrument of vaginal endoscope, typical of endoscopes to which the protector sheath of the present invention is applicable. However, it is to be understood that the present invention is not limited to this type of endoscope and can be applied to endoscopes of other types as long as they are equipped with an insertion instrument having, successively from its proximal to fore end, a manipulating or gripping head, a rigid rod section, a flexible rod section, an angle section and a tip end section.

In FIG. 1, indicated at 1 is a manipulating or gripping head of an endoscopic insertion instrument, at 2 an insertion rod and at 3 a light guide cable. The insertion rod 2 is provided with a large-diameter rigid rod section 2a, a small-diameter rigid rod section 2b, a flexible rod section 2c, an angle section 2d and a tip end section 2e successively from its proximal end which is connected to the manipulating head 1. A rotational operating ring 4 is provided at the joint of the large- and small-diameter rigid rod sections 2a and 2b, so that the insertion rod portions forward of the small-diameter rod section 2b can be turned about the longitudinal axis of the insertion instrument when the rotational operating ring 4 is turned with a finger or fingers. In this instance, the rotational operating ring 4 is provided with a knurled operating portion 4b around the circumference of a ring body proper 4a for secure contact with operator's fingers.

Figure 2:
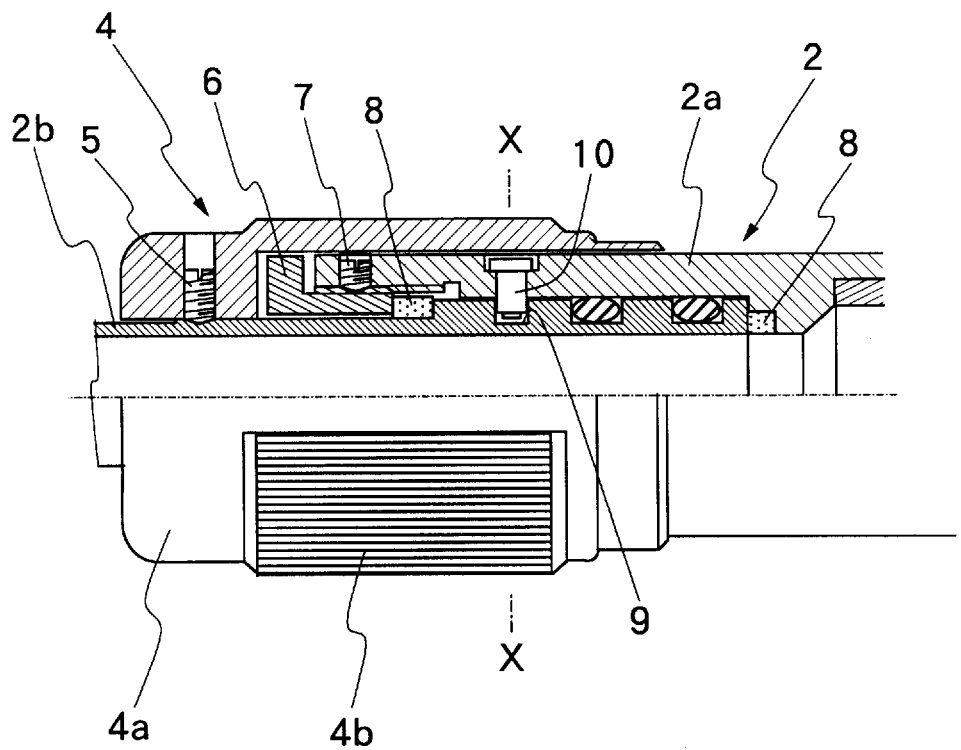
FIG. 2 is a partly sectioned schematic view of a rotary joint coupling large- and small-diameter rigid rod sections of an endoscopic insertion instrument relatively rotatably with each other.
Figure 3:
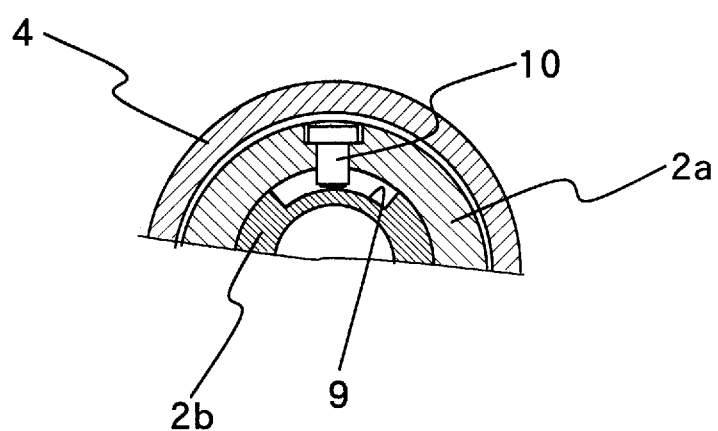
FIG. 3 is a fragmentary sectional view taken on line X—X of FIG. 2.

More specifically, in this case, the large- and small-diameter rigid rod sections 2a and 2b are coupled with each other through a rotary joint mechanism which is arranged as shown in FIGS. 2 and 3 to permit the relative rotational movements of the two rigid rod sections. As seen in these figures, the narrow rigid rod section 2b is hermetically fitted in the thick rigid rod section 2a over a predetermined fit length. The rotational operating ring 4 is fixed to the narrow rigid rod section 2b by means of set screw 5. Fitted on the fore end of the thick rigid rod section 2a is a stopper ring 6 which is fixed to the rigid rod section 2a by means of a set screw 7. Further, a slip bearing 8 is interposed between the fitted end of the narrow rigid rod section 2b and a stepped wall on the inner periphery of the thick rigid rod section 2a and also between the stopper ring 6 and a stepped wall on the outer periphery of the narrow rigid rod section 2b. The narrow rigid rod section 2b is provided with a circumferential groove 9 through a predetermined angle to receive therein a connector pin 10 which is provided on the part of the thick rigid rod section 2a. Consequently, upon turning the rotational operating ring 4, its rotation is followed by the narrow rigid rod section 2b within a predetermined rotational range which is determined by the angular range of the circumferential groove 9 on the narrow rigid rod section.

Figure 4:
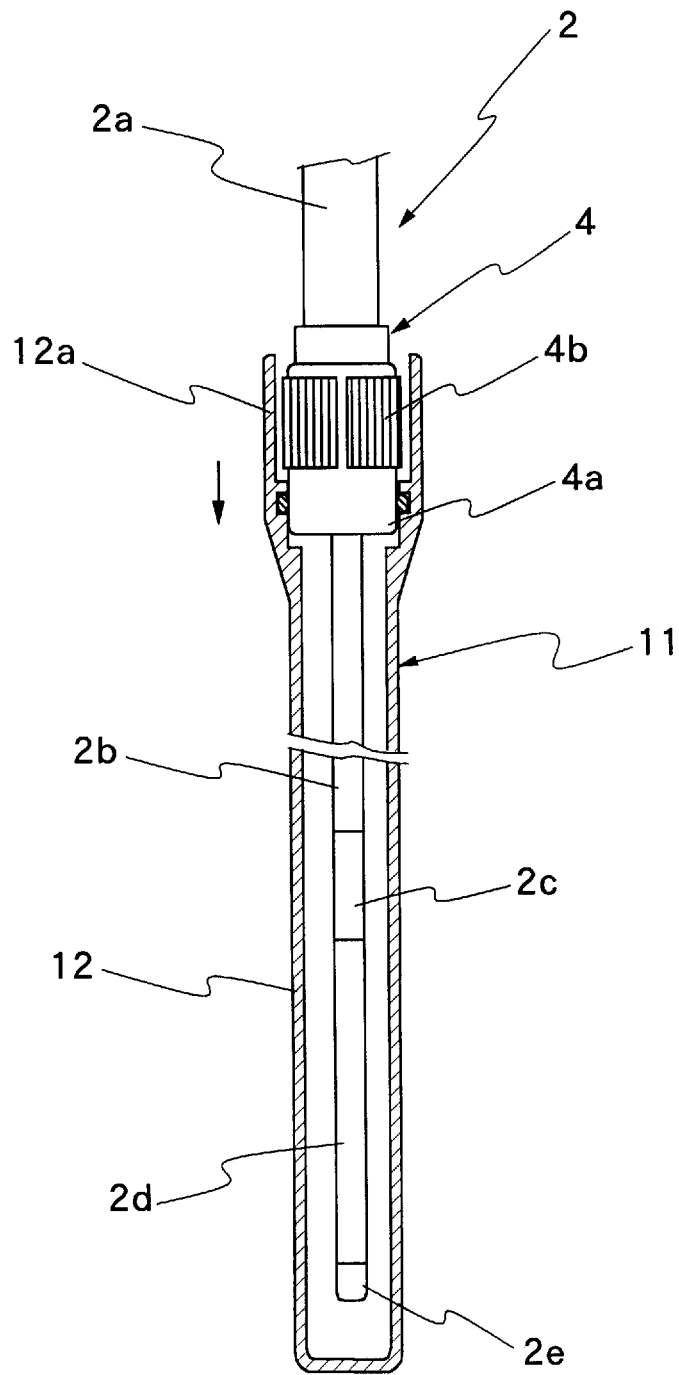
FIG. 4 is a longitudinal sectional view of a protector sheath embodying the invention, which is fitted on an endoscopic insertion instrument.
Figure 5:
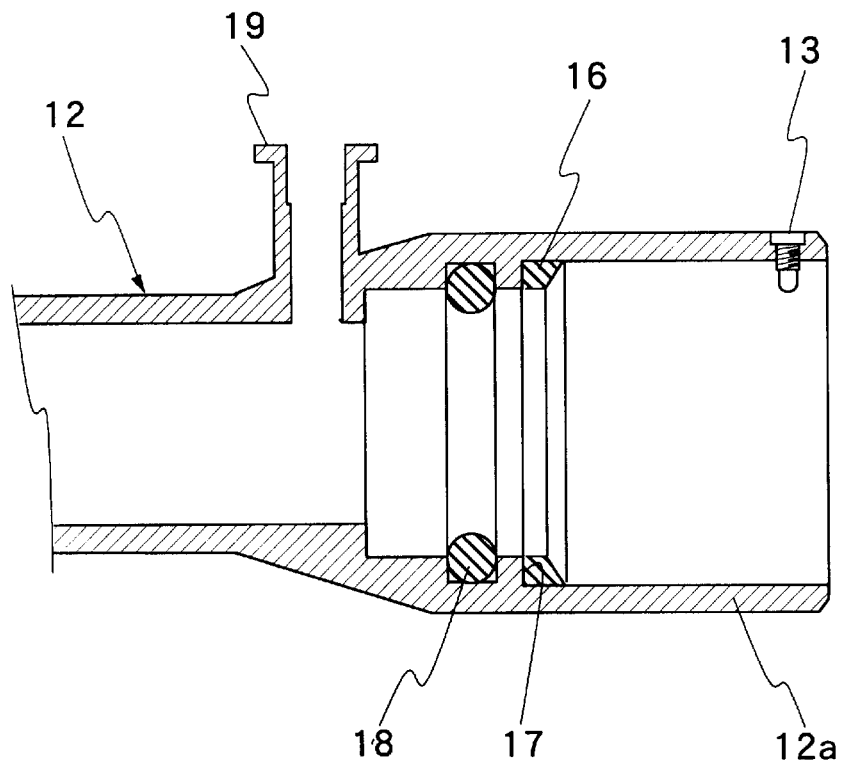
FIG. 5 is an enlarged sectional view of the protector sheath of FIG. 4, taken in a 90° shifted position.

As shown in FIGS. 4 and 5, a protector sheath 11 is hermetically fitted on the endoscopic insertion instrument, enshrouding the insertion rod 2 from its fore end up to a point on the proximal side of the rotational operating ring 4 on the thick rigid rod section 2a. The body of the protector sheath 11 is in the form of a bottomed hollow and tubular case of a predetermined length, which is formed of a rigid material like metal or hard plastics or a resilient material like rubber. The material for the protector sheath 11 is preferred to have excellent chemical resistance in case a disinfectant liquid is filled into the sheath as will be described hereinlater, but inexpensive hard plastics may be used for the sheath body in case it is discarded after use. As mentioned hereinbefore, in case a resilient material like rubber is used for the protector sheath, it should have a certain degree of stiffness to ensure satisfactory protective functions of the sheath.

Figure 6:
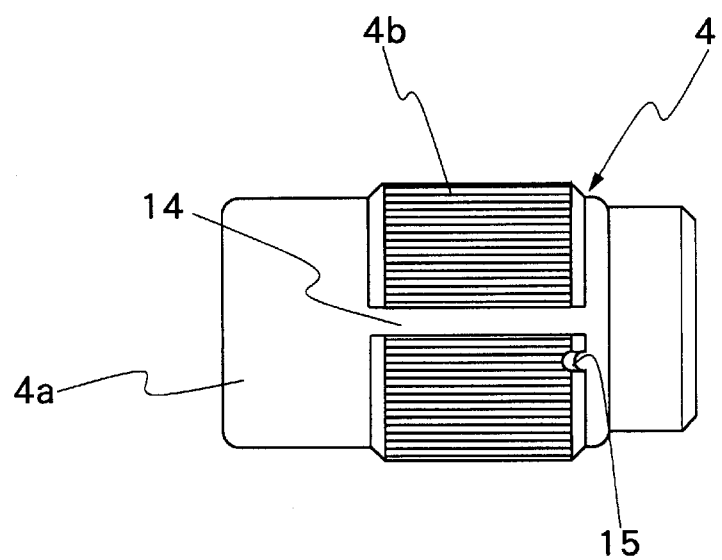
FIG. 6 is a schematic outer view of a rotational operating ring.

As mentioned above, the body 12 of the protector sheath 11 to be removably fitted on the endoscopic insertion rod 2 is preferably dimensioned to enshroud the insertion rod 2 at least from its fore end up to the operating member 4b on the rotational operating ring 4. For this purpose, the sheath body 12 is provided with an enlarged diameter portion 12a, with an enlarged inside diameter, at its proximal open end which serves as an entrance and exit opening for the insertion rod 2. On or in the vicinity of the enlarged diameter portion 12a, the protector sheath body 12 is provided with a stopper mechanism which releasably stops the sheath body 12 in position on the insertion rod 2 when fitted thereon. The stopper mechanism includes one or a plural number of stopper projections in the form of screw studs 13. The screw stud 13 is protruded into the protector sheath body 12 by a predetermined length from the inner peripheral surfaces of the latter for engagement with the rotational operating ring 4 on the thick rigid rod section 12a of the insertion rod 12. To this end, as shown in FIG. 6, the rotational operating ring 4 is provided with an indented or recessed trap or traps 15, along with and in the vicinity of an axial guide groove 14, at its proximal end, that is, at its end on the side of the operating head 1 of the endoscopic insertion instrument. The projection length of the screw studs 13 from the inner peripheral surface of the sheath body 12 is adjusted smaller than the depth of the axial guide groove 14. The indented trap 15 is brought into and out of engagement with the projected inner end of the screw studs 13 as will be described hereinlater.

Fitted in the enlarged diameter portion 12a of the protector sheath body 12 is a resilient ring 16 of a predetermined axial thickness, which is formed of a resilient material such as rubber or the like. This resilient ring 16 is compressed when the protector sheath is fitted on the endoscopic insertion rod 2, so that, by elastic regaining or restoring force of the resilient ring 16, the protector sheath body 12 is biased in the arrowed direction in FIG. 4. Accordingly, the resilient ring 16 serves as a biasing means acting on the protector sheath body 12 and holding the screw stud 13 in engagement with the indented trap 15. More specifically, the resilient ring 16 is fitted in position on the inner periphery of the enlarged diameter portion 12a by abutting engagement with a stopper wall 17 which is in turn formed in such a position that, when the protector sheath body 12 is fitted on the insertion rod 2, the stopper wall 17 and the proximal end of the rotational operating ring 4 are spaced from each other by a gap which is narrower than the axial thickness of the resilient ring 16 in natural or uncompressed state. Therefore, the resilient ring 16 is compressed by this dimensional difference when the protector sheath body 12 is fitted on the insertion rod 2. A seal member 18 in the form of an O-ring is also fitted on the inner periphery of the enlarged diameter portion 12a at a position immediately on the front side of the resilient ring 16, for abutting engagement with the ring body 4a of the rotational operating ring 4.

Further on the front side of the seal member 18, the protector sheath body 12 is provided with a disinfectant inlet port 19 which is disconnectibly connectible either to a syringe or other disinfectant feed means or to a plug or other closure means (both not shown). Accordingly, after fitting the protector sheath 12 on the endoscopic insertion rod 2, a disinfectant container can be connected to the disinfectant inlet port 19 to fill in a disinfectant liquid, and afterwards the disinfectant inlet port 19 is hermetically closed with a plug, leaving the disinfectant liquid in a sealed state within the protector sheath body 12. When fitted on the insertion rod 2, the interior of the protector sheath body 12 is held in a hermetically sealed state. Therefore, in order to supply a disinfectant liquid into the protector sheath body 12 on the insertion rod 2, it is necessary to provide a closable respiratory hole in a suitable position although not shown in the drawings.

In use, the insertion rod 2 of the endoscope, without the protector cover 11 as shown in FIG. 1, is introduced into an intracavitary portion of interest to carry out an endoscopic examination in the manner well known in the art. It is after the examination that the protector sheath 11 is fitted on the insertion rod 2, which has been extracted from the patient body.

In endoscopic examinations, the insertion rod 2 is introduced into the patient body normally up to a point somewhere in the flexible rod section 2c from its distal end section 2e although it could be inserted more deeply up to a fore end portion of the narrow rigid rod section 2b in rare cases. In other words, except for limited small areas at the fore end of the narrow rigid rod section 2b, the narrow and thick rigid rod sections 2b and 2a of the insertion rod 2 are always kept out of contact with the patient body during examinations. Now, for fitting the protector sheath body 12 in position on the extracted insertion rod 2, one needs to straighten the angle section 2d of the rod, if it is in a bent form, and to turn the screw stud 13 on the protector sheath body 12 into a position in agreement with the angular position of the guide groove 14 on the operating member 4b of the rotational operating ring 4.

Then, the protector sheath body 12 is fitted on the insertion rod 2 up to a position where the rotational operating ring 4 is completely covered under the enlarged diameter portion 12a of the sheath body 12. In so doing, the protector sheath 11 can be put on quite smoothly because one can firmly grip any part of the insertion rod 2 rearward of the fore end of the narrow rigid rod section 2b. Confirming that the screw stud 13 on the protector sheath body 12 has reached a position on the proximal side of the rotational operating ring 4 past the axial guide groove 14, the sheath body 12 is turned slightly about the rotational operating ring 4 to bring the screw stud 13 into face to face relation with the indented trap 15 on the latter. In this state, the resilient ring 16 is in a compressed state, urging the protector sheath body 12 axially in the forward direction of the endoscopic insertion rod 2. Accordingly, upon relieving the protector sheath body 12 of a rearward pushing force, the inner projected end of the screw stud 13 on the enlarged diameter portion 12a is urged in the forward direction and caught in the indented trap 15, thus fixedly stopping and locking the protector sheath body 12 on the insertion rod 2.

Now, the narrow rigid rod section 2b, flexible rod section 2c, angle section 2d and tip end section 2e of the endoscopic insertion rod 2 are completely enshrouded under the protective sheath body 12, so that, even if the protector sheath body 12 is hit against a nearby object while the endoscope is being carried for transfer to a place with endoscopic cleaning facilities, there is little possibility of the collisional impacts being transmitted directly to the insertion rod 2, especially to the joint portion between narrow rigid rod section 2b and the flexible rod section 2c which is most vulnerable to deformations and buckling damages. Besides, since contaminated portions of the insertion rod 2, particularly fore end portions of the insertion rod 2, which had been introduced into the patient body, are completely covered in an unexposed state, one can grip any part of the endoscope in carriage without contaminating his or her own hand. Even if the endoscope should come into contact with a nearby object while being carried in hand or when put on a desk or the like before cleaning, there is no possibility of transferring contaminant to the contacting object.

At a cleaning station, contaminants on the insertion rod are washed off by immersion in water in a washing sink which is supplied with running water. At this time, the protector sheath 11 is removed from the insertion rod 2 by unlocking and releasing the screw stud 13 from the indented trap 15 on the rotational operating ring 4 on the insertion rod 2 by a procedure inverse to the above-described locking operation. The protector sheath 11 may be removed while in an immersed state or prior to immersion in cleaning water. In consideration of possibilities that the interior surfaces of the protector sheath 11 might have been contaminated by contact with fore end portions of the insertion rod 2, it is desirable to wash the protector body 12 with water simultaneously with or separately from the cleaning of the endoscopic insertion rod 2. However, usually it is not necessarily required to wash the protector sheath 11 as carefully as the endoscope itself.

After washing and drying, the endoscope may be put in a suitable storage place. However, it is desirable to disinfect the washed endoscope, particularly fore end portions of the insertion rod 2 into a completely cleaned and sanitized state. For this purpose, the protector sheath 11 is fitted on the insertion rod 2 again, and a disinfectant liquid is pumped into the protector sheath body 12 from a disinfectant container which is connected to the fluid inlet port 19 on the protector sheath body 12. As soon as the protector sheath body 12 is filled with the disinfectant liquid, the fluid supply port 19 is closed with a plug means. By immersion in the disinfectant liquid over a predetermined time period, the insertion rod portions forward of the narrow rigid rod section are completely sterilized in preparation for next use.

Figure 7:
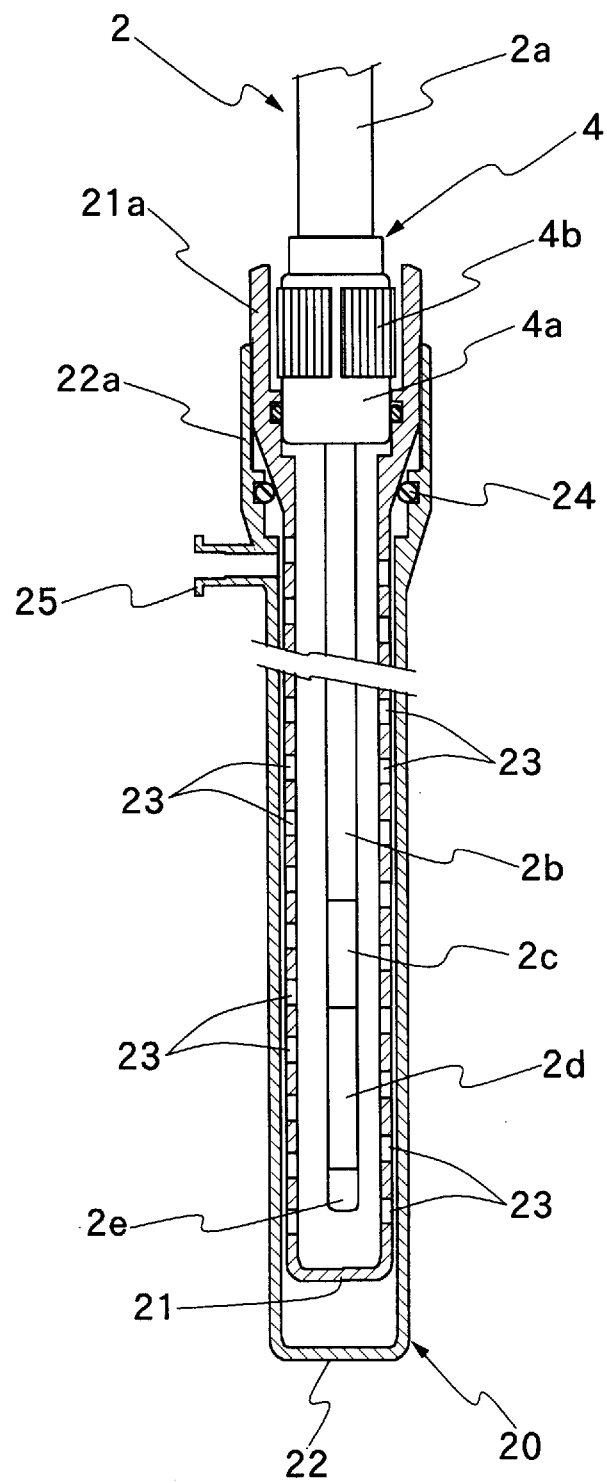
FIG. 7 is a view similar to FIG. 4 but showing another embodiment of the protector sheath according to the present invention.

As described above, in the first embodiment of the invention, the protector sheath 11 has to be put on and off the endoscopic insertion rod twice in order to perform the functions of both protection against collisional impacts and complete disinfection of the insertion rod. To avoid this, the protector sheath body may be arranged to have a double-sheath structure having first and second or inner and outer sheaths as shown at 20 in FIG. 7.

More specifically, in this instance, the first or inner sheath 21 is arranged substantially in the same manner as the protector sheath body 12 in the foregoing first embodiment, including an enlarged diameter portion 21a which is provided with identical counterparts of the screw stud 13, resilient ring 16 and seal member 16 although not shown in the drawing. In this case, however, the first sheath body 21 is perforated with a plural number of fluid circulation holes 23 to permit inward and outward flows therethrough of a cleaning liquid and a disinfectant liquid. The number and size of the holes 23 are determined within a range which would prohibit direct contact of the insertion rod 2 with other objects even in collisional situations while permitting sufficient circulation therethrough of a fluid medium like disinfectant liquid. The enlarged diameter portion 21a of the inner sheath body 21 is externally provided with an external screw portion. Nevertheless, in this case, the inner sheath body 21 is not provided with any fluid inlet port like the above-described disinfectant inlet port 19.

On the other hand, the second or outer sheath body 22 which is fitted over the first sheath body 21 has an inside diameter appreciably larger than the outside diameter of the first sheath body 21, so that a gap space is formed between the first and second sheath bodies 21 and 22. The second sheath body 22 is provided with an internal screw portion 22a in its base end portion for threaded engagement with the external screw on the enlarged diameter portion 21a of the first sheath body 21. The second sheath body 22 is in the form of a bottomed tubular case which contains no holes in its walls, and provided with a seal member 24 on the front side of the internal screw portion 22a for hermetically sealing the gap space between the inner and outer sheath bodies 21 and 22, and a disinfectant inlet port 25 on the front side of the seal member 24.

After an endoscopic examination, the first protector sheath 21 alone is fitted on the insertion rod 2 of an used endoscope prior to picking up and bringing same to a washing sink at a cleaning station, thereby protecting the flexible rod portion against buckling damages particularly in its end portions adjoining rigid rod sections of the insertion rod on the way to the cleaning station. Accordingly, the first sheath body 21 plays the role of protecting the endoscopic insertion rod, which is a primary function of the protector sheath body 12 of the above-described first embodiment. Then, at the cleaning station, the endoscopic insertion rod is immersed in a cleaning liquid within a washing sink together with the first protector sheath 21. At this time, the endoscopic insertion rod is washed by contact with the cleaning liquid which flows into and out of the first protective sheath 21 through the perforated holes 23. The endoscope, with the first protector sheath 21 still on the insertion rod 2, is then lifted up out of the sink and, after draining the cleaning liquid off the first protector sheath 21, the second protector sheath 22 is fitted on and tightly coupled with the first sheath body 21 by way of the internal screw portion 22a. After coupling together the two sheath bodies 21 and 22, a disinfectant liquid is poured into the protector sheath through the disinfectant inlet port 25. The disinfectant inlet port 25 is hermetically closed with a plug to hold the disinfectant liquid in the protector sheath in a sealed state. Accordingly, the second sheath body 22 plays the role of a disinfectant reservoir container, which is a secondary function of the protector sheath body 12 of the first embodiment.

The just-described arrangements of the second embodiment, which do not require to put on or off the protector sheath before and after a washing treatment, contribute to make the washing and disinfection of the insertion rod easier as compared with the first embodiment.

What is claimed is:

1. In a protector sheath for an insertion instrument of an endoscope having an increased diameter portion in proximity of a proximal end of an insertion rod to be introduced into a body cavity, said protector sheath being adapted to enclose the insertion rod forward of the increased diameter portion and to hold a cleaning or disinfectant liquid for the insertion rod, said protector sheath comprising:

an elongated sheath body having a length larger than that of the insertion rod forward of the increased diameter portion and being closed at a distal end thereof;

a stopper projection provided on said sheath body in the vicinity of an open end proximal thereof configured to lock said protector sheath on the insertion rod by interlocking engagement with a groove provided on the increased diameter portion on the part of the insertion rod;

a seal member provided on said sheath body on the front side of said stopper projection and adapted to be abutted against the increased diameter:

a liquid supply port provided on said sheath body on the front side of said seal member to supply a cleaning or disinfectant liquid into closed spaces formed on said sheath body by abutting engagement of said seal member with the increased diameter portion.

2. A protector sheath as defined in claim 1, wherein said sheath body is formed of a material selected from the group consisting of metals, hard plastics, soft plastics, and natural or synthetic rubber materials.

3. A protector sheath as defined in claim 1, wherein said stopper comprises:

a projection provided on an inner peripheral surface of said sheath body and adapted to be engageable with the insertion rod.

4. A protector sheath for protecting an endoscopic insertion instrument having an insertion rod, comprising:

a sheath body which has opposite open and closed ends along a longitudinal direction of said sheath body and into which the insertion rod of the endoscopic insertion instrument can be introduced from the open end, said sheath body being adapted to form a closed space for accommodating a fluid for cleaning the insertion rod when the insertion rod is introduced into said sheath body:

a stopper which is provided in a vicinity of the open end of said sheath body and detachably attaches said sheath body to the insertion rod, said stopper comprising a stopper projection provided on an inner peripheral surface of said sheath body and adapted to be engageable with the insertion rod: and a biasing device which presses said stopper projection toward the insertion rod.

5. A protector sheath for protecting an endoscopic insertion instrument having an insertion rod, comprising:

a first sheath body which has opposite open and closed ends along a longitudinal direction of said first sheath body and into which the insertion rod of the endoscopic insertion instrument can be introduced from the open end, said first sheath body having fluid circulating holes;

a second sheath body into which said first sheath body can be detachably introduced so as to form a closed space inside of said second sheath body for accommodating a fluid for cleaning the insertion rod when the insertion rod is introduced into said first sheath body; and a stopper which is provided in a vicinity of the open end of said first sheath body and detachably attaches said first sheath body to the insertion rod, said stopper including a stopper projection provided on said first sheath configured to lock said first sheath on the insertion instrument by interlocking engagement with a groove provided on an increased diameter portion of the insertion instrument.

6. A protector sheath as defined in claim 5, wherein said second sheath body has a fluid inlet port for supplying the fluid in the closed space.

* * * * *